United States Patent
Harada et al.

(10) Patent No.: US 9,284,249 B2
(45) Date of Patent: Mar. 15, 2016

(54) METHOD FOR EXTRACTING ASYMMETRIC β-DIKETONE COMPOUND FROM β-DIKETONE COMPOUND

(71) Applicant: TANAKA KIKINZOKU KOGYO K.K., Tsukuba-shi, Ibaraki (JP)

(72) Inventors: Ryosuke Harada, Tsukuba (JP); Toshiyuki Shigetomi, Tsukuba (JP); Satoshi Miyazaki, Tsukuba (JP); Masayuki Saito, Tsukuba (JP)

(73) Assignee: Tanaka Kikinzoku Kogyo K.K., Chiyoda-ku, Tokyo (JP)

( * ) Notice: Subject to any disclaimer, the term of this patent is extended or adjusted under 35 U.S.C. 154(b) by 0 days.

(21) Appl. No.: 14/438,963

(22) PCT Filed: Oct. 17, 2013

(86) PCT No.: PCT/JP2013/078132
§ 371 (c)(1),
(2) Date: Apr. 28, 2015

(87) PCT Pub. No.: WO2014/069240
PCT Pub. Date: May 8, 2014

(65) Prior Publication Data
US 2015/0291497 A1    Oct. 15, 2015

(30) Foreign Application Priority Data
Oct. 29, 2012 (JP) .................................. 2012-237909

(51) Int. Cl.
*C07C 45/80* (2006.01)
(52) U.S. Cl.
CPC ...................................... *C07C 45/80* (2013.01)
(58) Field of Classification Search
CPC ....................................................... C07C 45/80
USPC ......................................................... 568/410
See application file for complete search history.

(56) References Cited

FOREIGN PATENT DOCUMENTS

| | | |
|---|---|---|
| JP | 2001-163818 A | 6/2001 |
| JP | 2003-166058 A | 6/2003 |
| JP | 2003-267908 A | 9/2003 |
| JP | 2005-023065 A | 1/2005 |
| JP | 2005-336178 A | 12/2005 |
| JP | 2008-037765 A | 2/2008 |
| JP | 4054215 B2 | 2/2008 |
| JP | 4097979 B2 | 6/2008 |
| JP | 4746141 B2 | 8/2011 |

OTHER PUBLICATIONS

JP International Search Report, Application No. PCT/JP2013/078132, Dec. 25, 2013.
Adams et al., "The Acylation of Methyl Ketones with Aliphatic Esters by Means of Sodium Amide. Synthesis of β-Diketones of the Type RCOCH2COR", Journal of the American Chemical Society, Apr. 1944, pp. 1220-1222, vol. 66.
Swamer et al., "Claisen Acylations and Carbethoxylations of Ketones and Esters by Means of Sodium Hydride", Journal of the American Chemical Society, Aug. 1949, pp. 1352-1356, vol. 72.

*Primary Examiner* — Sikarl Witherspoon
(74) *Attorney, Agent, or Firm* — Orrick Herrington & Sutcliffe, LLP

(57) ABSTRACT

The present invention provides a method of extracting an asymmetric β-diketone compound from a β-diketone compound containing at least one symmetric β-diketone compound mixed in the asymmetric β-diketone compound, and the method includes the step (A) of adjusting a pH of a mixed solution of the β-diketone compound and water at 11.5 or more and dissolving the β-diketone compound into water to form a β-diketone compound solution and the step (B) of subsequently adjusting the pH of the β-diketone compound solution at 9.5 or less and recovering the asymmetric β-diketone compound of Chemical Formula 1 separated from the β-diketone compound solution. The present invention further includes at least either (a) a step of setting the upper limit of the pH of the mixed solution to 12.5 to form a β-diketone compound solution in the step (A) and bringing the β-diketone compound solution into contact with a hydrophobic solvent or (b) a step of setting the lower limit of the pH of the β-diketone compound solution to 8.0 in the step (B).

7 Claims, 1 Drawing Sheet

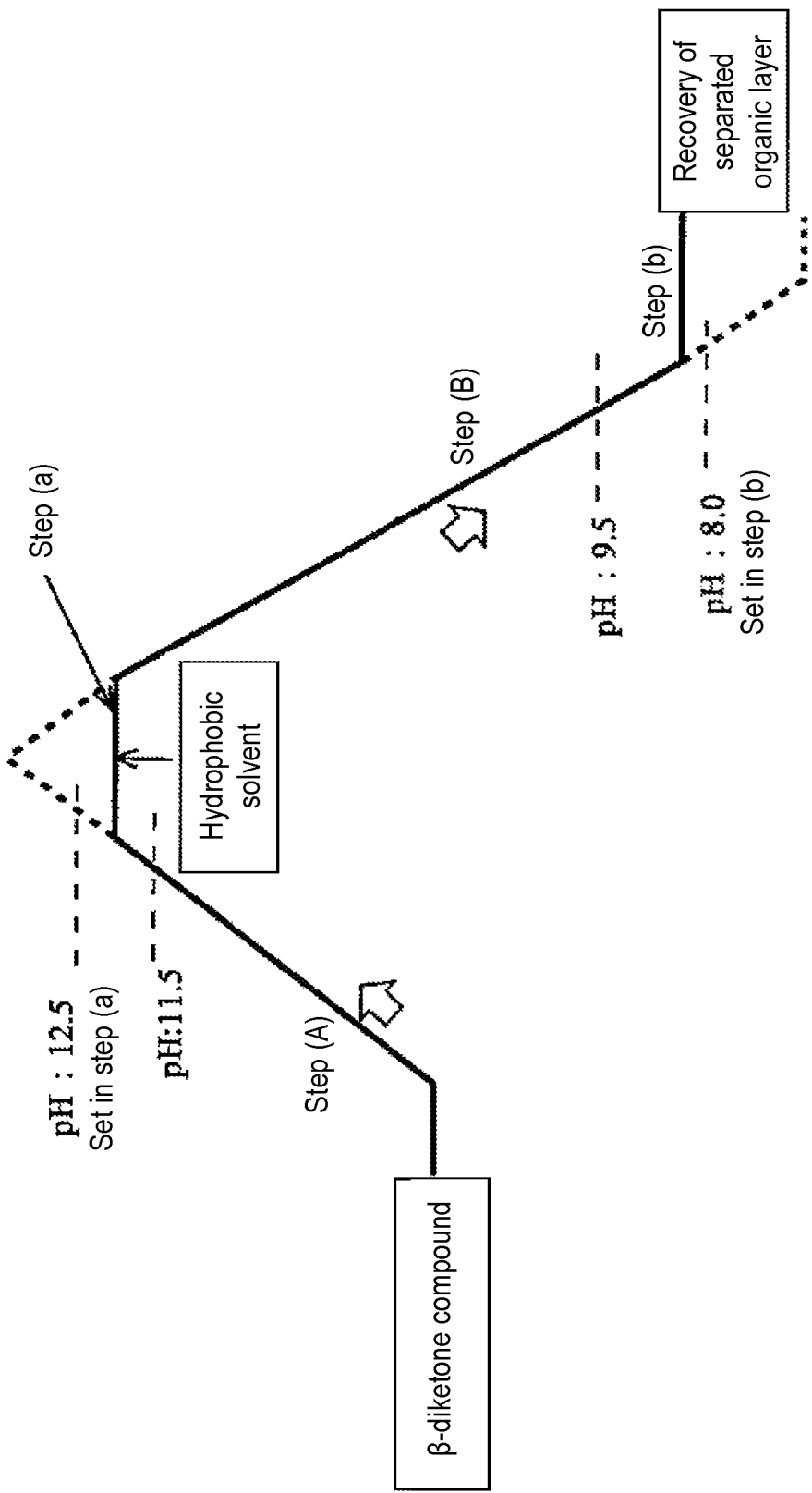

METHOD FOR EXTRACTING ASYMMETRIC β-DIKETONE COMPOUND FROM β-DIKETONE COMPOUND

TECHNICAL FIELD

The present invention relates to a method of extracting an asymmetric β-diketone compound that is useful as, for example, a precursor of a raw material for a chemical vapor deposition method. Specifically, the invention relates to a method of selectively extracting and purifying an asymmetric β-diketone compound from a β-diketone compound containing a symmetric β-diketone compound and the asymmetric β-diketone compound in mixture.

BACKGROUND ART

A β-diketone compound had been formerly used for applications such as additives and fragrances of synthetic resins. However, in recent years, utilization of the β-diketone compound as a precursor of an organic metal compound that is a raw material for formation of a metallic thin film by chemical vapor deposition methods (such as CVD method and ALD method) is attracting attention. Examples of an organic metal compound in which β-diketones are coordinated, which is useful as a raw material for a chemical vapor deposition method, include organic metal compounds described in Patent Documents 1 to 3. These organic metal compounds are obtained by coordinating 2 to 3 β-diketones to a core metal such as Ru and Ir. These organic metal compounds contain β-diketones as ligands, thereby having advantages such as favorable adhesiveness when a thin film is formed and preferable reactivity to a specific reaction gas (such as hydrogen).

[Chemical Formula 1]

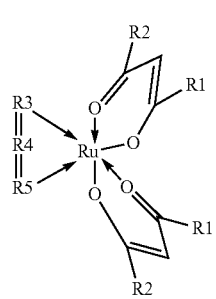

[Chemical Formula 2]

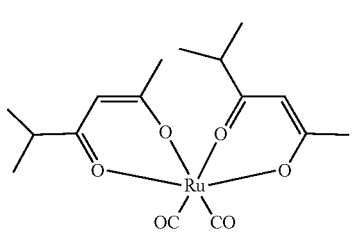

[Chemical Formula 3]

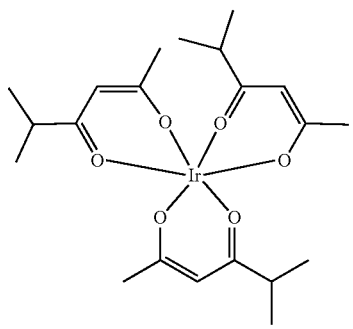

In the above organic metal compounds, those having different substituents of β-diketones ($R_1$ and $R_2$ in Chemical Formula 1) are assumed to be preferable. This is because organic metal compounds having different $R_1$ and $R_2$ can be formed into a liquid state at normal temperature and handling properties of a raw material in a step of thin film formation by a chemical vapor deposition method are preferable (refer to Patent Document 1). In this respect, the organic metal compounds of Chemical Formulas 2 and 3 have different substituents such as a methyl group and an ethyl group as substituents of β-diketones. Then, in order to synthesize organic metal compounds in which such asymmetric β-diketones are coordinated, a β-diketone compound to be a precursor is also required to have an asymmetric property.

Herein, as a method for producing an asymmetric β-diketone compound, basically, a synthesis reaction similar to a symmetric β-diketone compound can be used, and a desired reaction substance having two types of substituents may be used in this reaction. Examples of the method include a synthesis method by a condensation reaction between an ester compound and a ketone compound according to the reaction formula described below (Patent Document 4, Non-patent Documents 1 and 2). In this synthesis method, starting materials (ester compound and ketone compound) are easily obtained, reaction steps are also easy and simple, and the synthesis method is therefore generally used.

[Chemical Formula 4]

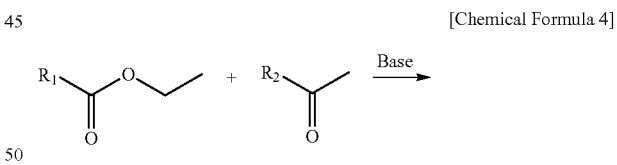

In addition, besides the above synthesis method, there is a synthesis reaction of using a β-ketoester as a starting raw material according to the following formula. This synthesis reaction is a method of reacting a β-ketoester and a carboxylic acid halide or a carboxylic anhydride and obtaining a β-diketone compound by a dealkoxycarbonylation reaction of the obtained intermediate product.

[Chemical Formula 5]

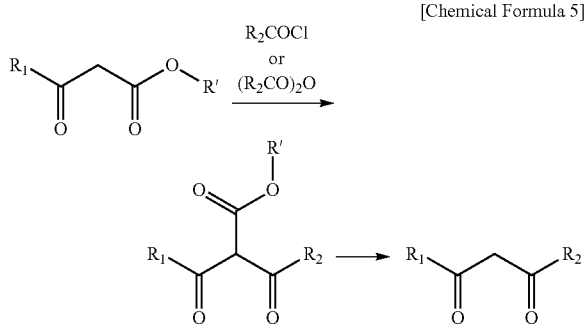

RELATED ART DOCUMENTS

Patent Documents

Patent Document 1: JP 4097979 B2
Patent Document 2: JP 4746141 B1
Patent Document 3: JP 4054215 B2
Patent Document 4: JP 2005-023065 A

Non-Patent Documents

Non-patent Document 1: T. Adams and Charles R. Hauser, The Acylation of Methyl Ketones with Aliphatic Esters by Means of Sodium Amide Synthesis of β-Diketones of the Type $RCOCH_2COR^1$, J. Am. Chem. Soc., 1944 (vol. 66), p. 1220-1222.

Non-patent Document 2: Frederic W. Swamer and Charles R. Hauser, Claisen Acylation and Carbethoxylations of Ketones and Esters by Means of Sodium Hydride, J. Am. Chem. Soc., 1950 (vol. 72), p. 1352-1356.

SUMMARY OF THE INVENTION

Problems to be Solved by the Invention

However, according to the present inventors, a β-diketone compound obtained by the above synthesis method includes symmetric β-diketone compounds of Chemical Formulas 7 and/or 8 as byproducts in addition to an asymmetric β-diketone compound (Formula 6) which is the object of production.

[Chemical Formula 6]

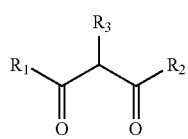

[Chemical Formula 7]

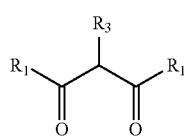

[Chemical Formula 8]

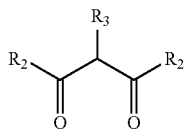

Then, when an organic metal compound is produced by means of an asymmetric β-diketone compound containing a symmetric β-diketone compound in mixture as a precursor, not only an organic metal compound in which asymmetric β-diketones are coordinated but also an organic metal compound in which symmetric β-diketones are coordinated are produced. An organic metal compound still containing an organic metal compound in which symmetric β-diketones are coordinated in mixture does not show desired physical properties and film formation characteristics and thus needs to be removed; however, not only a production cost for the removal step is generated but also loss of a metal for the removed organic metal compound is caused. As described above, in the case of an organic compound using a noble metal, its loss cannot be ignored, which leads to a cost increase of raw materials for chemical vapor deposition, and consequently to a cost increase of a device to which a thin film is applied.

Accordingly, it can be said that, for a β-diketone compound containing a symmetric β-diketone compound and an asymmetric β-diketone compound in mixture, the symmetric β-diketone compound is removed before its use and the asymmetric β-diketone compound may be extracted, but it is not easy. A symmetric β-diketone compound and an asymmetric β-diketone compound have close physical properties such as a boiling point, and effective separation and purification are difficult in a vapor deposition method that is a general separation and purification means. In addition, column chromatography capable of separation extraction with high precision cannot respond to mass production and leads to a cost increase of an asymmetric β-diketone compound.

The present invention is attained based on the above backgrounds, and a purpose is to provide a method of extracting an asymmetric β-diketone compound from a β-diketone compound, which is synthesized in any method, effectively in a level capable of mass production.

Means for Solving the Problems

The present inventors made intensive investigations in order to solve the above problems and found that a gap of solubility to water (hydrophilicity) is caused as a difference between an asymmetric β-diketone compound and a symmetric β-diketone compound in a β-diketone compound.

A β-diketone compound is a compound having hydrophilicity that is changed by a pH. Then, the pH is formed into an alkaline side in a mixed solution with water, thereby easily deprotonating to be ionized and hydrophilicity tends to increase. This is a tendency shown in both of an asymmetric β-diketone compound and a symmetric β-diketone compound and, according to the present inventors, there is a relationship as described below between a solubility of an asymmetric β-diketone compound of Chemical Formula 6 described above and a solubility of a symmetric β-diketone compound of Chemical Formulas 7 and 8 described above (Substituents $R_1$ and $R_2$ of a β-diketone compound are alkyl groups and the number of carbon atoms is $R_1 < R_2$. $R_3$ is hydrogen or an alkyl group.)

[Chemical Formula 9]

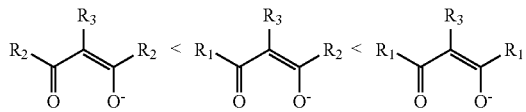

The above relationship means that a symmetric β-diketone compound of Chemical Formula 8, which has substituent $R_2$ with the larger number of carbon atoms than substituent $R_1$, is the lowest in a solubility in the alkaline condition (hydrophobicity). Thus, a hydrophobic solvent is brought into contact with a β-diketone compound solution in the alkaline condition and the symmetric β-diketone compound of Chemical Formula 8 having high hydrophobicity is thus transferred to this hydrophobic solvent and can be removed.

Then, the above relationship of small and large solubility does not change even when a pH of a β-diketone compound solution varies. Thus, when the pH of the solution is decreased and shifted to the neutral side, the asymmetric β-diketone compound of Chemical Formula 6 having a lower solubility than the symmetric β-diketone compound of Chemical Formula 7 is separated from the solution first. Then, by setting the pH value in this step within a favorable range, the asymmetric β-diketone compound can be recovered while the symmetric β-diketone compound of Chemical Formula 7 is remained to be dissolved.

The present inventors focused on fluctuation in hydrophilicity by a pH of a β-diketone compound and on magnitude relationship of a degree of solubility between an asymmetric β-diketone compound and a symmetric β-diketone compound, as explained above. Then, the present inventors found that an asymmetric β-diketone compound with a high purity can be purified by swinging up and down a pH of a mixed solution of a β-diketone compound to be treated under strict supervision and separating and extracting a symmetric β-diketone compound or an asymmetric β-diketone compound from the solution in each pH region, and conceived of the present invention.

That is, the present invention is a method of extracting an asymmetric β-diketone compound of Chemical Formula 10 from a β-diketone compound containing at least either a symmetric β-diketone compound of Chemical Formula 11 or a symmetric β-diketone compound of Chemical Formula 12, which is mixed in the asymmetric β-diketone compound, the method including the steps of (A) and (B) described below, and further including at least either the step (a) or (b) described below.

Step (A): a step of adjusting a pH of a mixed solution of the β-diketone compound and water at 11.5 or more and dissolving the β-diketone compound into water to form a β-diketone compound solution; and step (B): a step of subsequently adjusting the pH of the β-diketone compound solution at 9.5 or less and recovering the asymmetric β-diketone compound of Chemical Formula 10 separated from the β-diketone compound solution.

Step (a): a step of setting the upper limit of the pH of the mixed solution to 12.5 to form a β-diketone compound solution in the step (A) and bringing the β-diketone compound solution into contact with a hydrophobic solvent to thus transfer the symmetric β-diketone compound of Chemical Formula 12 into the hydrophobic solvent.

Step (b): a step of setting the lower limit of the pH of the β-diketone compound solution to 8.0 in the step (B) and separating and recovering the asymmetric β-diketone compound of Chemical Formula 10 separated from the β-diketone compound solution.

[Chemical Formula 10]

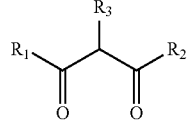

[Chemical Formula 11]

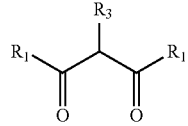

[Chemical Formula 12]

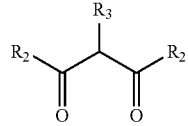

(In each chemical formula, $R_1$ and $R_2$, which are substituents, are alkyl groups, and have a relationship of the number of carbon atoms in $R_1$ < the number of carbon atoms in $R_2$. $R_3$ is hydrogen or an alkyl group.)

Hereinbelow, the present invention will be more specifically explained. First, for a β-diketone compound to be treated in the present invention, its synthesis step is not particularly limited. Accordingly, a β-diketone compound obtained by any of the above synthesis method by a condensation reaction between an ester compound and a ketone compound and the synthesis method of using a β-ketoester as a starting raw material is employed. In addition, β-diketone compounds synthesized by a method other than these two synthesis methods may also be used.

As a symmetric β-diketone compound contained in a β-diketone compound to be treated, two types of symmetric β-diketone compounds can be considered according to a substituent, and only one type may be contained or both types may be contained. This is because selectivity of a generation reaction of a symmetric β-diketone compound that is a side reaction cannot be controlled in a synthesis of an asymmetric β-diketone compound. Note that when only one of the symmetric β-diketone compounds is contained as described below, or when a content of one of the symmetric β-diketone compounds is small, separation and removal of the symmetric β-diketone compound may not be carried out in order to simplify the steps.

In addition, although a β-diketone compound having various alkyl groups ($R_1$ and $R_2$) is an object in the present invention, and the number of carbon atoms is not limited, the invention is useful for extraction of an asymmetric β-diketone compound having an alkyl group with preferably 1 to 4 carbon atoms. $R_1$ and $R_2$ are different alkyl groups and have a relationship of the numbers of carbon atoms of $R_1$ < $R_2$. Each of $R_1$ and $R_2$ is selected from a methyl group, an ethyl group, a propyl group (n-propyl group, isopropyl group), a butyl group (n-butyl group, isobutyl group, tert-butyl group, sec-butyl group), and a combination that satisfies the above relationship of the numbers of carbon atoms is preferable. In addition, a substituent $R_3$ is hydrogen or an alkyl group, and when the substituent $R_3$ is an alkyl group, the number of carbon atoms is also not limited, but preferably from 1 to 4.

Since the present invention involves a treatment of a solvent system, a reaction solution after synthesis of the above asymmetric β-diketone compound may be used as an object to be treated. However, a synthesis reaction of an asymmetric β-diketone compound accompanies generation of other organic substances in addition to symmetric and asymmetric β-diketone compounds in many cases, and removal of these other organic substances is difficult in the separation method of the present invention, which uses a gap in solubility. Therefore, a β-diketone compound in a state in which the other organic substances are removed after a synthesis reaction is preferably used as an object to be treated. This preferable β-diketone compound to be treated has a total content of symmetric and asymmetric β-diketone compounds of 80 to 100% by weight. This is because when the β-diketone compound contains about 20% of the other organic substances, the other organic substances can be removed by suitably carrying out distillation or the like, after extraction of the asymmetric β-diketone compound.

The present invention has a basic constitution including the steps of (A) using a β-diketone compound obtained by any method as described above as an object to be treated, mixing the β-diketone compound into water to form a mixed solution and setting the pH within an alkaline region of 11.5 or more, and (B) decreasing the pH of the β-diketone compound solution to 9.5 or less after the step (A).

The step (A) is, as described above, a step of dissolving a β-diketone compound (including symmetric and asymmetric) into water using an increase in hydrophilicity due to rise of a pH of the β-diketone compound. Herein, the reason of setting the lower limit value of the pH to 11.5 is because the β-diketone compound cannot be completely dissolved without setting the pH to 11.5 or higher, resulting in giving an adverse effect on a final yield of the asymmetric β-diketone compound. A preferable lower limit value of the pH is 12.0. On the other hand, the upper limit value of the pH set in the step (A) is determined depending on whether removal of a symmetric β-diketone compound of Chemical Formula 12 by the step (a) is conducted or not. Then, when the treatment of the step (a) is not carried out, the upper limit of the pH is not particularly limited, but is preferably set to about 13.5 in consideration of saving on a base added or the like for pH adjustment.

As a means for increasing a pH in the step (A), adding a metal hydroxide to a solution is preferable. This is because a metal hydroxide is a strong alkali and has a high solubility to water, and pH adjustment is easy. Specific additives include lithium hydroxide, sodium hydroxide, potassium hydroxide, rubidium hydroxide and cesium hydroxide, all of which are hydroxides of alkaline metals.

The step (B) is a step of lowering hydrophilicity of a β-diketone compound by decreasing the pH of the β-diketone compound solution generated in the step (A) to thus separate the asymmetric β-diketone compound from the solution. The reason of setting the upper limit of the pH to 9.5 is because the β-diketone compound may be dissolved in the solution with a pH exceeding 9.5, resulting in decreasing the yield of the asymmetric β-diketone compound. A preferable upper limit value of the pH is 9.0. On the other hand, the lower limit value of the pH set in the step (B) is different depending on whether the lower limit value of the pH set in the step (b) is applied or not. When the pH set in the step (b) is not applied, the lower limit of the pH is not particularly limited, but is preferably set to about 7.0 in consideration of saving an acid to be added or the like for pH adjustment.

As a means for decreasing the pH of the solution in the step (B), adding at least any of hydrochloric acid, sulfuric acid and perchloric acid to the solution is preferable. These are inexpensive and strong acids, and pH adjustment is easy.

A solution having a pH decreased by this the step (B) contains an asymmetric β-diketone compound that is in a state of being separated as an organic layer and the purified asymmetric β-diketone compound can be obtained by recovering the organic layer. For this recovery, solvent extraction using a hydrophobic solvent may be carried out.

The present invention has a basic constitution including the above steps (A) and (B), and the upper limit and the lower limit of pH values in each step are determined depending on presence or absence of the steps (a) and (b).

The step (a) is a step of removing a symmetric β-diketone compound of Chemical Formula 12, which contains a substituent having the large number of carbon atoms. In this step, a β-diketone compound solution is generated by setting the upper limit value of the pH to 12.5, and a hydrophobic solvent is brought into contact with the solution, thereby transferring the symmetric β-diketone compound of Chemical Formula 12, which has the lowest hydrophilicity, into the hydrophobic solvent to be thus removed. Setting the upper limit of the pH to 12.5 is because hydrophilicity of the symmetric β-diketone compound of Chemical Formula 12, which is an object to be removed, is also increased with a pH exceeding 12.5, and removal with a hydrophobic solvent thus becomes difficult. The upper limit value of the pH is more preferably 12.2. A hydrophobic solvent brought into contact with the β-diketone compound solution is preferably any of pentane, hexane, heptane, petroleum ether, cyclohexane, benzene, toluene, xylene, diethyl ether, diisopropyl ether, dichloromethane and chloroform. A contacting time (method) in this process is preferably 5 minutes or more. A treatment of contacting a β-diketone compound solution and a hydrophobic solvent may be once, but is preferably conducted twice or more.

The step (b) is a step of setting the lower limit value of a pH in order to prevent accompaniment of a symmetric β-diketone compound of Chemical Formula 11, which contains a substituent having the small number of carbon atoms, when the pH of the β-diketone compound solution generated in the step (A) is decreased to separate an asymmetric β-diketone compound from the solution. Since hydrophilicity of the symmetric β-diketone compound of Chemical Formula 11 is higher than that of the asymmetric β-diketone compound of Chemical Formula 10, when the pH value that is decreased in the step (B) is higher than the pH value of separating the symmetric β-diketone compound of Chemical Formula 11, the symmetric β-diketone compound is resulted in remaining in the solution. The step (b) is to use this phenomenon and to set the lower limit value of the pH in a solution for separating the symmetric β-diketone compound of Chemical Formula 11 to 8.0. With pH lower than 8.0, the symmetric β-diketone compound of Chemical Formula 11 is also separated from the solution. A preferable lower limit value of a pH is 8.5.

For a temperature of a solution in each of the above steps, the steps can be carried out at normal temperature without particular limitation. Then, a recovered asymmetric β-diketone compound may be directly provided as a raw material for production of a complex, and a post treatment such as distillation may also be conducted. Distillation is a preferable post treatment since impurities such as organic substances other than a β-diketone compound can be completely removed. As the condition of distillation, distillation with a reduced pressure is preferably carried out at a pressure of 100 Pa and a temperature from 30 to 35° C.

As understood from the above explanation, presence or absence of operations of the step (a) and the step (b), that is, presence or absence of setting the upper limit of the pH and presence or absence of contacting with a hydrophobic solution in the step (A) and presence or absence of setting the lower limit of the pH in the step (B) are determined by a constitution of a β-diketone compound to be treated. This is explained by FIG. 1. When both of symmetric β-diketone compounds of Chemical Formulas 11 and 12 are contained in a β-diketone compound to be treated, treatments of both of the steps (a) and (b) are carried out (pH is adjusted as shown by a solid line in FIG. 1). When a symmetric β-diketone compound of Chemical Formula 12 is only contained in a β-diketone compound to be treated, or when an amount of a symmetric β-diketone compound of Chemical Formula 11 is very small, an asymmetric β-diketone compound can be extracted only by conducting the treatment in the step (a) (pHs are adjusted along with a solid line in the step (A) and a dotted line in the step (B)). When a symmetric β-diketone compound of Chemical Formula 11 is only contained in a β-diketone compound to be treated, or when an amount of a symmetric β-diketone compound of Chemical Formula 12 is very small, the step (a) is not necessary and an asymmetric β-diketone compound can be extracted by decreasing a pH immediately after dissolution of the β-diketone compound in the step (A) (pH is not particularly limited as long as it is 11.5 or more), in consideration of the lower limit value of the pH set in the step (b) (pHs are adjusted along with a solid line in the step (A) and a dotted line in the step (B)). Note that the criterion of "when an amount is very small" in the above description includes a case of having a content of any of symmetric β-diketone compounds of 0.1% or less in a β-diketone compound to be treated.

Effect of the Invention

As explained above, according to the present invention, an asymmetric β-diketone compound can be effectively extracted from a β-diketone compound produced by any production method. Furthermore, according to the present invention, a purity of an organic metal compound in which asymmetric β-diketone is coordinated can be secured and there is no loss of metals, and the like. Therefore, reduction in a cost of thin film formation by a chemical vapor deposition method can be intended.

BRIEF DESCRIPTION OF THE DRAWINGS

FIG. 1 is a diagram illustrating pH fluctuation in the β-diketone solution in the present invention.

MODE FOR CARRYING OUT THE INVENTION

First Embodiment

Herein, 5-methyl-2,4-hexanedione of Chemical Formula 13 ($R_1$: $C_2H_5$, $R_2$: $CH_3$) was synthesized as an asymmetric β-diketone compound by using various base catalysts according to the synthesis method of Chemical Formula 4.

[Chemical Formula 13]

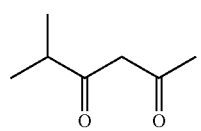

Then, symmetric β-diketone compounds of Chemical Formulas 14 and 15 (Formula 14: 2,4-pentanedione wherein both $R_1$ and $R_2$ are $CH_3$, Formula 15: 2,6-dimethyl-3,5-heptanedi- one wherein both $R_1$ and $R_2$ are $C_2H_5$) were separated from the synthesized β-diketone compound to extract an asymmetric β-diketone compound.

[Chemical Formula 14]

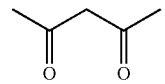

[Chemical Formula 15]

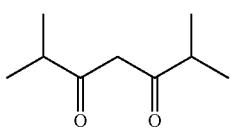

A synthesis of 5-methyl-2,4-hexanedione is carried out by reacting a diisopropyl ether and 3-methyl-2-butanone by Chemical Formula described below according to a reaction of Chemical Formula 4 as described above.

[Chemical Formula 16]

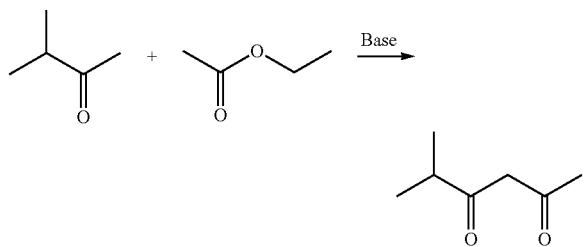

In the present embodiment, three base catalysts of $NaNH_2$, NaH and t-BuOK (potassium tert-butoxide) were used as base catalysts. In addition, a synthesis was carried out with $NaNH_2$ at a plural (4) reaction temperatures. Synthesis steps using each base catalyst will be explained below.

(I) Synthesis of β-Diketone Compound
(i) Synthesis of Using $NaNH_2$ as Base

A 1 L-three neck flask was charged with 150 mL of a diisopropyl ether, 36.2 g (40.2 mL) of ethyl acetate and 15.3 g of $NaNH_2$. While stirring the mixture, 33.7 g of 3-methyl-2-butanone (42.0 mL) was added with a dropping funnel to be reacted at reaction temperatures of 0° C., 25° C., 50° C. and 70° C. for 1.5 hours. A part of the reaction solution after this synthesis reaction was collected and concentrated to be analyzed and, as a result, the resultant containing about 60% of a β-diketone compound (containing both of symmetric and asymmetric β-diketone compounds) was obtained.

In order to purify a β-diketone compound from the reaction solution after the synthesis reaction, thereto was added 100 mL of water to dissolve a salt generated by the reaction, and a separated organic layer was removed. The pH of the reaction solution in the stage of adding water was 13. Then, 30 mL of hexane was added to the residual aqueous layer, and extraction and washing were carried out twice. Next, 15% hydrochloric acid was added to the aqueous layer to adjust the pH at 7.0. The organic layer (β-diketone compound) generated and separated by this pH operation was recovered. Then, the recovered product was analyzed by gas chromatography to measure a ratio of an asymmetric β-diketone compound (Formula 13) and symmetric β-diketone compounds (Formula 14 and Formula 15). The β-diketone compounds synthesized herein were assumed to be No. 1 to No. 4 corresponding to the reaction temperatures (0° C., 25° C., 50° C. and 70° C.). Note that about 90% of the recovered product is constituted with the β-diketone compound.

(ii) Synthesis of Using NaH as Base

A 1 L-three neck flask was charged with 150 mL of a diisopropyl ether, 36.2 g (40.2 mL) of ethyl acetate and 17.1 g of NaH (55% oil dispersion). The mixture was maintained at 50° C. with stirring, and thereto was added 20.1 g (25.0 mL) of 3-methyl-2-butanone with a dropping funnel over 1 hour. The reaction solution was reacted at 50° C. for 1.5 hours.

After completion of the reaction, 5 mL of ethanol was added and stirred, and unreacted NaH was treated to be removed. Then, in the same manner as a use of the above $NaNH_2$ as a base, a salt in the reaction solution was dissolved into water, and extracted and washed, and the organic layer (β-diketone compound) generated and separated by conducting a pH operation was recovered. The β-diketone compound synthesized herein was assumed to be No. 5.

(iii) Synthesis of Using t-BuOK as Base

A 1 L-three neck flask was charged with 150 mL of a diisopropyl ether, 36.2 g (40.2 mL) of ethyl acetate and 43.8 g of t-BuOK. Thereto was added 33.7 g (42.0 mL) of 3-methyl-2-butanone with a dropping funnel with stirring and the mixture was reacted at 25° C. for 1.5 hours. After completion of the reaction, the organic layer (β-diketone compound) was recovered from the reaction solution in the same procedure as described below. The β-diketone compound synthesized herein was assumed to be No. 6.

Table 1 shows analytical results of ratios of asymmetric β-diketone compounds and symmetric β-diketone compounds by gas chromatography for the No. 1 to No. 6 β-diketone compounds produced above.

TABLE 1

| No. | Base | Reaction temperature | Yield of β-diketone | Asymmetric | Symmetric | |
|---|---|---|---|---|---|---|
| 1 | $NaNH_2$ | 0° C. | 25% | 99.80 | 0.12 | 0.08 |
| 2 | | 25° C. | 40% | 99.12 | 0.67 | 0.21 |
| 3 | | 50° C. | 40% | 99.15 | 0.58 | 0.27 |
| 4 | | 70° C. | 8% | 99.58 | 0.05 | 0.37 |
| 5 | NaH | 50° C. | 62% | 99.57 | 0.40 | 0.03 |
| 6 | t-BuOK | 25° C. | 37% | 99.50 | 0.45 | 0.05 |

From Table 1, 99% or more of a β-diketone compound synthesized by each base catalyst and reaction temperature is constituted with an asymmetric β-diketone compound that is the production object. However, it is found that symmetric β-diketone compounds are contained in all synthesis examples. Reasonably, in generation of symmetric β-diketone compounds, two types of symmetric β-diketone compounds are not constantly generated in the same level. That is, in No. 4, a generation amount of a symmetric β-diketone compound of Chemical Formula 14 is very small and generation of a symmetric β-diketone compound of Chemical Formula 15 is large. Adversely, in No. 5 and No. 6, a generation amount of a symmetric β-diketone compound of Chemical Formula 15 is very small, and generation of a symmetric β-diketone compound of Chemical Formula 14 is large.

In addition, when this synthesis result was studied in consideration of the yield, in the case of improving the yield, a countermeasure of adjusting a reaction temperature or selecting NaH as a base can be considered and, in this case, a ratio of an asymmetric β-diketone compound tends to decrease (from contrast between No. 1 and No. 2, and contrast between No. 1 and No. 5). Therefore, when a yield is required to be particularly increased, necessity of removing a symmetric β-diketone compound arises in the synthesized β-diketone compound.

Furthermore, it was found from the result in Table 1 that in a production step of a general asymmetric β-diketone compound (synthesis step and purification step), suppression of accompaniment of a symmetric β-diketone compound is inevitable. That is, the above production steps include a purification step of washing a salt generated after a synthesis reaction and separating and purifying the salt. In these steps, a reaction solution at the time of adding water for dissolution of the salt is alkaline (pH 13), and also added with hydrochloric acid later to set the pH to 7. This operation is for the purpose of removing organic substances other than β-diketone in advance and similar to the constitution of the invention of the present application (however, the pH range is different from a pH range that is set in at least either the step (a) or (b) of the present invention). However, even when such a pH adjustment is carried out in the purification step, a symmetric β-diketone compound is included in the recovered β-diketone compound (Table 1). Accordingly, it can be confirmed that accompaniment of a symmetric β-diketone compound is inevitable in usual synthesis and purification steps.

(II) Purification of Asymmetric β-Diketone Compound

Extraction and purification of an asymmetric β-diketone compound were carried out on the produced No. 1 to No. 6 β-diketone compounds. Herein, purification was conducted on No. 1 having a relatively high ratio of an asymmetric β-diketone compound in a conventional distillation method, and purification was conducted on No. 2 to No. 6 in combination of the purification method according to the present invention and a distillation method. Purification steps for the No. 1 to No. 6 β-diketone compounds will be described in the following.

No. 1

Conventional Example

This β-diketone compound was purified by distillation. In the conditions in this purification, a pressure was 100 Pa and the temperature was from 30 to 35° C. An analysis was conducted after purification by gas chromatography and a content ratio of β-diketone was measured.

No. 2

An aqueous 8% sodium hydroxide solution was added to the recovered β-diketone compound to form an aqueous solution having pH 12. This aqueous solution was added with 20 mL of hexane and intensively stirred and the reaction solution was extracted, and the hexane layer was then removed. This extraction operation with hexane was carried out twice. The remained aqueous layer was added with 15% hydrochloric acid to set the pH to 8.8, and the separated organic layer was recovered and distilled to thus obtain an asymmetric β-diketone compound. Distillation was conducted under the same conditions as No. 1.

No. 3

No. 3 was distilled after carrying out the above extraction and purification of No. 2 twice. That is, a step of recovering an organic layer that was separated by addition of hydrochloric acid and adding an aqueous sodium hydroxide solution to the recovered organic layer again, and the like, was repeated to recover the separated organic layer and the organic layer was distilled. Distillation was conducted in the same conditions as No. 1.

No. 4

As described above, No. 4 had a very small generation amount of a symmetric β-diketone compound of Chemical Formula 14, which has the small number of carbon atoms, and a large generation amount of a symmetric β-diketone compound of Chemical Formula 15, which has the large number of carbon atoms. Thus, with this sample, a pH value at the time of addition of hydrochloric acid was set to a low value (pH adjustment based on the step (b) was not performed) while a step of extracting a symmetric β-diketone compound in an alkaline region was carried out (step (a)).

An aqueous 8% sodium hydroxide solution was added to the recovered No. 4 β-diketone compound to set the pH to 12. This aqueous solution was added with 20 mL of hexane and intensively stirred and the reaction solution was extracted, and the hexane layer was then removed (operated twice). The remained aqueous layer was added with 15% hydrochloric acid to adjust the pH to 7.0, and the separated organic layer was recovered and distilled.

No. 5 and No. 6

Each of Nos. 5 and 6 has a small generation amount of a symmetric β-diketone compound of Chemical Formula 15, which has the large number of carbon atoms. Thus, these samples were formed into an alkaline region to dissolve the β-diketone compounds, thereafter immediately decreasing the pH without extraction with hexane.

An aqueous 8% sodium hydroxide solution was added to the recovered β-diketone compound to set the pH to 12. Then, 15% hydrochloric acid was added to the solution to adjust the pH to 9.0, and the separated organic layer was recovered and distilled.

Table 2 shows analytical results of gas chromatography for the above purified asymmetric β-diketone compounds.

TABLE 2

| No. | Yields of β-diketone | | Ratio (%) | | |
|---|---|---|---|---|---|
| | Before purification | After purification | Asymmetric | Symmetric | Symmetric |
| 1 | 25% | 22% | 99.82 | 0.11 | 0.07 |
| 2 | 40% | 29% | 99.89 | 0.08 | 0.03 |
| 3 | 40% | 20% | >99.98 | <0.01 | <0.01 |
| 4 | 8% | 6% | 99.89 | 0.03 | 0.08 |
| 5 | 62% | 48% | 99.89 | 0.10 | 0.01 |
| 6 | 37% | 28% | 99.88 | 0.10 | 0.02 |

*A yield after purification is based on a raw material before a synthesis reaction.

In contrast to the analytical results before purification in Table 1, in Table 2, the purification steps including pH operation, which were carried out on No. 2 to No. 6, made a ratio of an asymmetric β-diketone compound increased and allowed a ratio of a symmetric β-diketone compound to be about 0.1%. On the contrary, there was a less change in a ratio of an asymmetric β-diketone compound in No. 1 that underwent purification only by a distillation method. Therefore, usefulness of the extraction and purification step by pH operation under strict supervision in the present invention can be confirmed. Note that although this extraction and purification step has a sufficient effect even once, repetition of the step twice or more makes it possible to obtain an asymmetric β-diketone compound close to about 100%. In addition, it was confirmed that only one of the steps (a) and (b) of the present invention was carried out on Nos. 4, 5 and 6, and an objective asymmetric β-diketone compound from which a symmetric β-diketone compound was removed can be obtained from all of Nos. 4, 5 and 6.

(III) Synthesis of Organic Metal Compounds

A synthesis of dicarbonyl-bis(5-methyl-2,4-hexandiketonato) ruthenium (II), which is an organic metal compound of Chemical Formula 2, was carried out with use of No. 2, No. 3 and No. 5 asymmetric β-diketone compounds after purification.

A 300 mL-three neck flask was charged with 4.8 g of dodecacarbonyl triruthenium, 9.0 g of a purified asymmetric β-diketone compound, and 100 mL of n-decane, and the mixture was heated and stirred under an argon atmosphere at 160° C. for 96 hours. After completion of the reaction, the reaction solution was distilled away under a reduced pressure with a rotary evaporator to obtain an organic ruthenium compound that is a light yellow liquid. Then, an analysis was conducted by gas chromatography to measure the constitution ratio of the produced compound. The result was shown in Table 3.

there is a possibility such that an organic metal compound as expected cannot be produced from such an asymmetric β-diketone compound. Accordingly, the extraction and purification step as the present invention can be useful for the purpose of obtaining an asymmetric β-diketone compound with a high purity as well as securing a yield.

The Second Embodiment

Herein, plural types of asymmetric β-diketones having different substituents $R_1$ and $R_2$ were synthesized and subjected to extraction and purification.

The synthesis reaction was followed by the synthesis reaction of Chemical Formula 4 in the same manner as in the first

TABLE 3

| | Ratio of β-diketone (%) | | |
| --- | --- | --- | --- |
| No. | 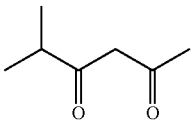 | 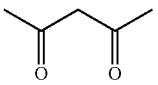 | 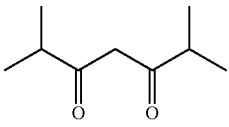 |
| 2 | 99.89 | 0.08 | 0.03 |
| 3 | >99.98 | <0.01 | <0.01 |
| 5 | 99.90 | 0.10 | 0.01 |

| | Ratio of Ru complex (%) | | |
| --- | --- | --- | --- |
| No. | 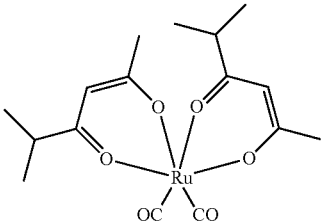 | 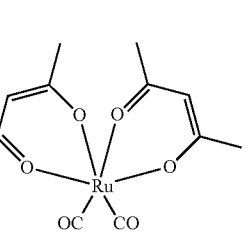 | 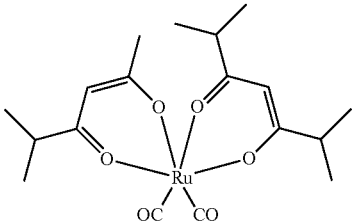 |
| 2 | 99.80 | 0.14 | 0.06 |
| 3 | >99.98 | 0.01 | <0.01 |
| 5 | 99.80 | 0.17 | 0.03 |

From Table 3, a purity of a synthesized organic metal compound (a ratio of an organic metal compound in which an asymmetric β-diketone compound is coordinated) corresponds to a constitution ratio of a β-diketone compound to be a raw material. Therefore, in order to effectively synthesize an organic metal compound without waste, it would be preferable to apply an asymmetric β-diketone compound that underwent such an extraction and purification step as the present invention.

Note that comparing a ratio of an organic metal compound in which a symmetric β-diketone compound is coordinated to a ratio of a symmetric β-diketone compound in raw materials, the ratio of the organic metal compound in which a symmetric β-diketone compound is coordinated was increased by a synthesis reaction. That is, it was found that the synthesis reaction also has a factor of increasing the ratio of the organic metal compound in which a symmetric β-diketone compound is coordinated. In this respect, a ratio of an asymmetric β-diketone compound can be made high to some extent only by the synthesis and purification step when a yield is sacrificed as the result of No. 1 in Table 1. However, for example, when the ratio barely satisfies the requested standard value, embodiment, and a corresponding ether compound having a substituent $R_1$ and ketone compound having a substituent $R_2$ were used as raw materials. Then, $NaNH_2$ was used as a base catalyst and the both compounds were allowed to be synthesized and reacted in the presence of the base catalyst. After the reaction, an extraction and separation operation was conducted for removal of an organic substance other than β-diketone similar to the first embodiment to thus recover a β-diketone compound.

Next, in the same manner as in the first embodiment, an aqueous sodium hydroxide solution was added to the recovered β-diketone compound to form the aqueous solution having pH 12 and the aqueous solution was extracted with hexane. A separated organic layer obtained when the residual aqueous layer was added with hydrochloric acid to set the pH to 8.8 was recovered. The purification operation described above was defined to be once. The recovered product was then distilled to obtain an asymmetric β-diketone compound. Distillation was also carried out in the same conditions as in the first embodiment. Table 4 shows the result of an analysis by gas chromatography conducted on a β-diketone compound having respective constituents $R_1$ and $R_2$ after purification.

TABLE 4

| No. | $R_1$ | $R_2$ | Yield of asymmetric β-diketone | Ratio of β-diketone (%) $R_1\text{-CO-CH}_2\text{-CO-}R_2$ | $R_1\text{-CO-CH}_2\text{-CO-}R_1$ | $R_2\text{-CO-CH}_2\text{-CO-}R_2$ |
|---|---|---|---|---|---|---|
| 7 | Methyl | n-Propyl | 45% | 99.87 | 0.11 | 0.02 |
| 8 | Methyl | Isobutyl | 44% | 99.95 | 0.04 | 0.01 |
| 9 | Methyl | sec-Butyl | 52% | 99.93 | 0.05 | 0.02 |
| 10 | Methyl | t-Butyl | 55% | 99.96 | 0.03 | 0.01 |
| 11 | Ethyl | t-Butyl | 53% | 99.90 | 0.08 | 0.02 |

It was found from Table 4 that even though substituents in an asymmetric β-diketone compound are different, the extraction and purification step of the present invention is useful.

INDUSTRIAL APPLICABILITY

The present invention is a method of effectively extracting and purifying an asymmetric β-diketone compound from a β-diketone compound obtained in any synthesis step. According to the present invention, a purity of an organic metal compound in which an asymmetric β-diketone is coordinated can be secured. Thereby, loss of a metal (precious metal) constituting an organic metal compound can be suppressed. The present invention can be conducive to reduction in a production cost of various devices for formation of a thin film by a chemical vapor deposition method.

The invention claimed is:

1. A method of extracting an asymmetric β-diketone compound of Chemical Formula 1 from a β-diketone compound comprising at least either a symmetric β-diketone compound of Chemical Formula 2 or a symmetric β-diketone compound of Chemical Formula 3, said symmetric β-diketone compound being mixed in the asymmetric β-diketone compound, the method comprising the steps of:

(A): adjusting a pH of a mixed solution of the β-diketone compound and water 11.5 or more and dissolving the β-diketone compound into water to form a β-diketone compound solution;

(B): subsequently adjusting the pH of the β-diketone compound solution 9.5 or less and recovering the asymmetric β-diketone compound of Chemical Formula 1 separated from the β-diketone compound solution; and at least either of:

(a): setting the upper limit of the pH of the mixed solution to 12.5 to form a β-diketone compound solution in the step (A) and bringing the β-diketone compound solution into contact with a hydrophobic solvent to thus transfer the symmetric β-diketone compound of Chemical Formula 3 into the hydrophobic solvent; or (b): setting the lower limit of the pH of the β-diketone compound solution to 8.0 in the step (B) and separating and recovering the asymmetric β-diketone compound of Chemical Formula 1 separated from the β-diketone compound solution:

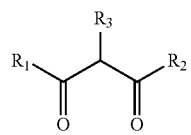

[Chemical Formula 1]

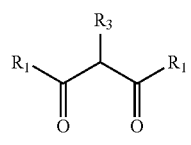

[Chemical Formula 2]

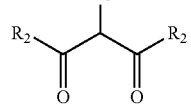

[Chemical Formula 3]

(in each chemical formula, $R_1$ and $R_2$, which are substituents, are alkyl groups, and have a relationship of the number of carbon atoms in $R_1$ < the number of carbon atoms in $R_2$, and $R_3$ is hydrogen or an alkyl group.).

2. The method of extracting an asymmetric β-diketone compound according to claim 1, wherein a step of adjusting the pH of the mixed solution in the step (A) comprises adding a metal hydroxide to the mixed solution.

3. The method of extracting an asymmetric β-diketone compound according to claim 1, wherein a step of adjusting the pH of the β-diketone compound solution in the step (B) comprises adding at least any of hydrochloric acid, sulfuric acid and perchloric acid to the solution.

4. The method of extracting an asymmetric β-diketone compound according to claim 1, wherein the hydrophobic solvent which is brought into contact with the β-diketone compound solution in the step (a) is any one of pentane, hexane, heptane, petroleum ether, cyclohexane, benzene, toluene, xylene, diethyl ether, diisopropyl ether, dichloromethane and chloroform.

5. The method of extracting an asymmetric β-diketone compound according to claim 2, wherein a step of adjusting the pH of the β-diketone compound solution in the step (B) comprises adding at least any of hydrochloric acid, sulfuric acid and perchloric acid to the solution.

6. The method of extracting an asymmetric β-diketone compound according to claim 2, wherein the hydrophobic solvent which is brought into contact with the β-diketone compound solution in the step (a) is any one of pentane, hexane, heptane, petroleum ether, cyclohexane, benzene, toluene, xylene, diethyl ether, diisopropyl ether, dichloromethane and chloroform.

7. The method of extracting an asymmetric β-diketone compound according to claim 3, wherein the hydrophobic solvent which is brought into contact with the β-diketone compound solution in the step (a) is any one of pentane, hexane, heptane, petroleum ether, cyclohexane, benzene, toluene, xylene, diethyl ether, diisopropyl ether, dichloromethane and chloroform.

* * * * *